(12) United States Patent
Tondra

(10) Patent No.: US 8,753,894 B2
(45) Date of Patent: Jun. 17, 2014

(54) INTEGRATED MEMBRANE SENSOR

(75) Inventor: Mark Christopher Tondra, Minneapolis, MN (US)

(73) Assignee: Diagnostic Biosensors, LLC, Minneapolis, MN (US)

( * ) Notice: Subject to any disclaimer, the term of this patent is extended or adjusted under 35 U.S.C. 154(b) by 1428 days.

(21) Appl. No.: 12/024,987

(22) Filed: Feb. 1, 2008

(65) Prior Publication Data

US 2008/0199971 A1 Aug. 21, 2008

Related U.S. Application Data

(60) Provisional application No. 60/887,609, filed on Feb. 1, 2007.

(51) Int. Cl.
*G01N 27/00* (2006.01)

(52) U.S. Cl.
USPC ........ 436/151; 436/149; 436/806; 435/287.1; 435/287.3; 422/68.1; 422/81; 422/82

(58) Field of Classification Search
USPC .............. 422/50, 51, 68.1, 82.05, 82.08, 186; 436/526, 501, 518, 514; 435/287.2, 435/287.1
See application file for complete search history.

(56) References Cited

U.S. PATENT DOCUMENTS 5,882,465 A * 3/1999 McReynolds ................. 156/285

FOREIGN PATENT DOCUMENTS

WO 2005/116661 A1 * 12/2005 ............. G01N 35/00

OTHER PUBLICATIONS

Millen et al., Giant magnetoresistive sensors and superparamagnetic nanoparticles: a chip-scale detection strategy for immunosorbent assays, Analytical Chemistry, vol. 77, No. 20, Oct. 15, 2005, 6581-6587.*

Peng et al., CMOS compatible integration of three-dimensional microfluidic systmes based on low-temperature transfer of SU-8 films, Hournal of Microelectromechanical Systems, vol. 15, No. 3, Jun. 2006, p. 708-716.*

Edelstein et al., The BARC biosensor applied to the detection of biological warfare agents, Biosensors & Bioelectronica 14 (2000) 805-813.*

* cited by examiner

*Primary Examiner* — Paul Hyun
*Assistant Examiner* — Robert Eom

(57) ABSTRACT

An integrated microelectronic sensor is provided in a disposable flow membrane sensing device. The integrated sensors detect electromagnetic effect labels in flow detection zones above the sensor in the membrane. The labels are small particles that give off a detectable electromagnetic signal. They are commonly used for isolating and quantifying biochemical targets of interest. The sensors are fabricated using planar integrated circuit technologies. Sensors can detect labels of several types including magnetic, electric, and photonic. These types all have in common the fact that the sensor detects the label at a distance. Magnetoresistive sensors for detecting magnetic labels, and photodiodes for detecting photonic labels are described.

A system for using the sensors is described. There are disposable cartridges with a backing that supports the sensors and membrane is described. The integrated sensor in the cartridge is designed to be discarded after use. Also, label excitation sources are provided. The multi sensor array chip can be configured in order to detect labels in multiple zones, and to monitor progress of flow down a strip of membrane. These multiple label detection zones, using sandwich assay techniques, can quantify analyte concentration for many types of analytical samples. Also, the membrane can be micropatterned in order to provide multiple or unusually shaped flow paths.

6 Claims, 10 Drawing Sheets

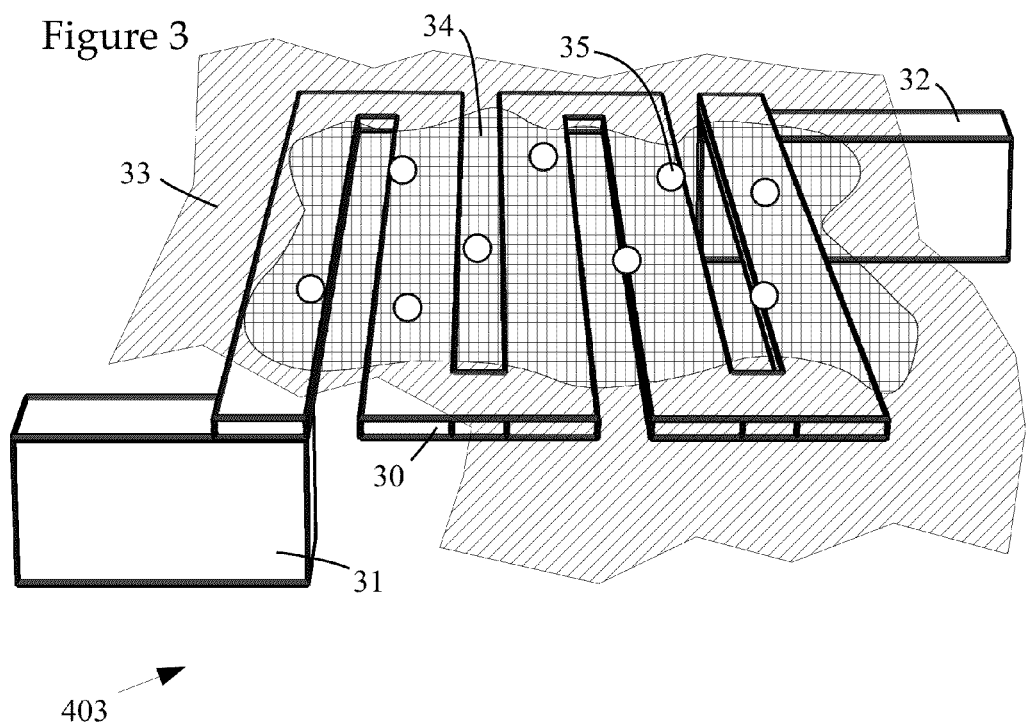
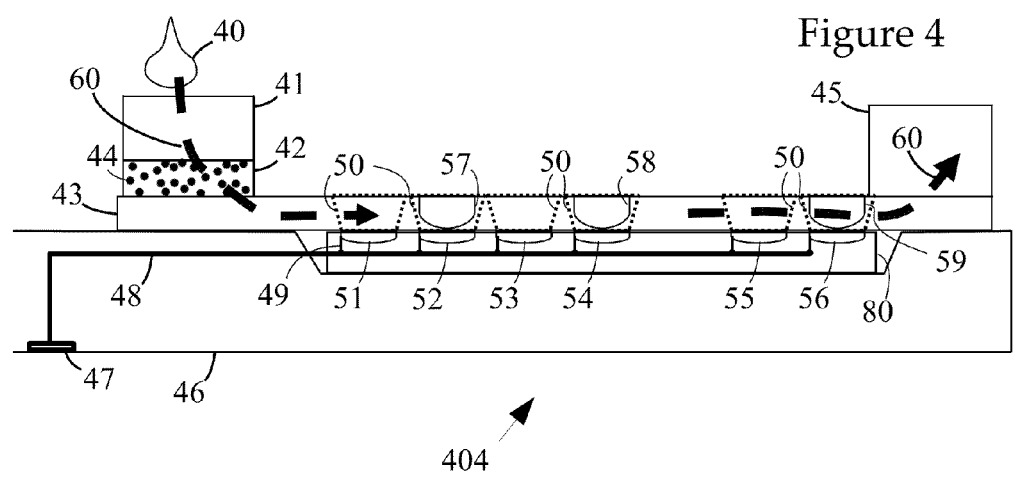

INTEGRATED MEMBRANE SENSOR

BACKGROUND OF THE INVENTION

The present invention describes novel devices and methods for detecting small labels using electronic sensors. Detecting the labels is of interest because they allow one to "see" or "quantify" tiny objects that would otherwise not be visible or detectable. For this to work, the labels must be "bound" to the object of interest. Or, sometimes, the labels are of interest in and of themselves. The object of interest could be a living cell or bacterium in the field of microbiology; a protein, nucleic acid, or antibody in the field of biochemistry; or almost any chemical species analyte.

In any case, the labels are very small particles. Here a particle is defined as a small physical object, typically with a longest dimension less than 1 mm. Many particles are roughly spherical, though there are also oblate spheroids, needles, cubes, and all manner of three dimensional shapes. The word "bead" is sometimes used to mean a particle.

A label is a specific kind of particle, one that gives off a measurable effect. It is this measurable effect that makes the label useful. In some cases, the measurable effect is light given off by a label dye. If enough label dye is present, the effect can be observed with the naked eye of a person looking at a jar of liquid. There are many cases, however, where the volume of fluid to be analyzed is very small, and the number of detectable objects is also very small, so the naked eye is not effective at detecting the object of interest. Furthermore, it is of great advantage to obtain data about the object of interest in the form of electronic digital data.

A step-by-step diagram is given in FIG. 1a to outline a process for using labels to generate electronic data.

Step 1. Energize the label.

Step 2. The label emits an effect.

Step 3. An electronic sensor receives the effect and converts it to an electronic signal.

Step 4. A detector circuit designed to work with the sensor converts the raw sensor signal to usable information. This data, then, can be used by a client (either another machine, or a person).

FIG. 1b shows, in simplified form, the physical components involved in performing the 4-step procedure 300 outlined in FIG. 1a.

An electromagnetic effect field 314 is defined as: a distribution, in space and time, of electric and/or magnetic fields. A key feature of these effects is that they can be detected at a distance. Common examples of sources for such electromagnetic effect fields include: an electron has a stray electric field in its vicinity; a label with a net magnetic moment has stray magnetic fields in its vicinity; a photon is a massless label having energy that is observable as coupled oscillating electric and magnetic fields.

An electromagnetic effect field label 313 is defined as: a label that, under certain circumstances, gives off an electromagnetic effect field. These kinds of labels are very useful for analytical work because the detector does not have to be in direct contact with the label.

An electromagnetic effect field sensor 315 is defined as: an electronic device which, upon the impingement of an electromagnetic effect field, induces an electronic signal in a detector circuit. Examples of electronic sensors, and the electromagnetic effect fields for which they are designed to respond are include: magnetoresistance, magnetic field; hall effect, magnetic field; electrodes, electric field; Field effect transistor (FET), electric field; photodiode, photon; inductor, magnetic field; respectively.

An example of an electronic sensor that is NOT an electromagnetic effect field sensor is one where the labels themselves are part of the sensor or detector circuit. For example, DNA is known to have a net electrical charge, and electrodes may be used to measure this charge by applying an electric field between the electrodes and measuring the resulting electrical current flow.

An electromagnetic effect field detector circuit 317 is defined as: a circuit specifically designed to create electronic data based on the output of the electromagnetic effect field electronic sensor. This circuit typically has electrical connections for: power supply, ground, positive and negative inputs for one or more electromagnetic effect field sensors plus possibly a third terminal for voltage biasing, an amplifier stage, and an analog-to-digital (ADC) conversion stage. It may also have switching circuits that enable the collection of electronic signals induced by a plurality of sensors. The electronic data from the detector circuit is typically in digital form.

A control system 318 is used to collect data from the detector circuit, analyze it, and pass the result to a client (either a person or separate system). Electrical and/or radio linkages are provided by connections 316 and 319.

An electromagnetic effect field label excitation source 311 is defined as: a source of electromagnetic energy 312 that may be imparted upon an electromagnetic effect field label 313 in such a way to induce that label to give off its specific electromagnetic effect field, 314. For example, some magnetic labels give off an electromagnetic effect field in direct proportion to the magnitude of the ambient magnetic field present at the label. A magnetic field excitation source provides a controlled addition to the ambient field. Another example: a fluorescence effect label gives off photons of a certain energy after being irradiated with photons of a specific higher energy. A photonic excitation source provides a controlled addition of specific higher energy photons to the fluorescence effect label.

Many labels give off some value of their electromagnetic effect field in the absence of any excitation source. Consequently, excitation source 311 is not always needed in a detection instrument 310. For example, some magnetic labels are permanently magnetized. Some molecules exhibit "autofluorescence".

Micro- and nano-magnetic labels are used commonly in biochemical assays as a means to capture, concentrate, and manipulate target analytes. They are also increasingly being used as detection labels for assay readout. These detection applications benefit from the large magnetic field signature generated by the labels when magnetized by an applied magnetic field, and by the very low incidence of background magnetic signals. Together, these features make magnetic detection attractive for a range of bioanalytical applications.

Several detection platforms can "see" and quantify magnetic labels, including magnetic microchips, SQUID magnetometers, scanning probes, and induction techniques. The focus of this disclosure is on the microchip-based devices. Magnetic microchip detectors are tiny, inherently rugged, and very low cost when produced in large quantities. They are made using manufacturing technology that is well developed. These sensors are incorporated into applications ranging from implantable medical devices, hearing aids, automobiles, and magnetic hard disk drives.

In-Vitro diagnostic applications present some exciting opportunities for magnetic microchip-based detection. Recent coil-based detector systems have generated highly quantitative results from lateral flow strip assays. The biochemical resolution of these assays is limited more by the lateral flow strip technology than the detection technology. Rapid improvement along several fronts (membrane properties and uniformity, magnetic label performance, micromanufactured substrates, etc.) make it likely that taking full advantage of magnetic detector capability will be desirable in the near future. Magnetic microchips have the potential to build on these accomplishments by increasing the numerical precision and spatial resolution of the assay readout. By providing highly multiplexed reader element, many spots and lanes can be quantified on the same strip. Furthermore, the ultra-low cost of detector chips makes them candidates for incorporation with the assay strip as a consumable item such as a disposable assay cartridge.

The combined qualities of readers and detectors make magnetic microchips ideally suited for de-centralized use, and in disposable assay formats. Already popular examples of applications like this are the pregnancy test (visual detection) and glucose monitoring (electrochemical). Both of these are already well served by the existing technology. But their technology will not be easily adapted to multiplexed assays, and to assays needing precision. Disposable magnetic assay chips, then, are likely to find their best use for small panels (in the range of 2 to 100 analytes) of immunoassays on a single-device. Markets for this technology include tests for food and water safety, agriculture, homeland defense, allergy, as well as many biomedical and veterinary medical uses.

The basis for using magnetic labels for biological assays is that they can be attached to the analyte through a biochemically specific binding mechanism. Assuming this capability exists for a given analyte, the challenge is then to count the labels in a way that provides data that is meaningful for the assay result. In order to illustrate the magnetic detection mechanisms, a simple example will be presented: detecting a single magnetic label bound to a magnetoresistive sensor sandwiching a captured analyte. This single-label example is not practical for most assay applications, but it provides a framework for understanding more realistic situations such as detecting large number of immobilized labels, and moving labels. Then are given some examples of detection of 2 dimensional label layers (e.g. surface immobilization assays), and finally 3 dimensional plugs (e.g. lateral flow strips).

Single Magnetic Label Detection.

Magnetic labels become magnetized (magnetization is induced in their volume) in the presence of an applied magnetic field. The direction of the magnetization is parallel to the applied field. The magnitude of magnetization is linearly proportional to the applied field. Thus, the magnetization is zero when the applied field is zero. (Note: we limit this discussion to paramagnetic labels. Some labels are ferromagnetic and/or permanent magnets, though these are not very commonly used.) The magnetic fields in the vicinity of a magnetic label are the sum of the externally applied field $H_{applied}$, and the stray fields from the label $H_{label}$. The $H_{applied}$ is usually from a magnetic field source that is far enough away to be considered spatially uniform in the vicinity of the label. But $H_{label}$ varies strongly both in magnitude and direction. These fields and a magnetized label are shown above a sensor in FIG. 1c. Typical magnetic field sources are passing electrical current through a wire or coil of wire, using a permanent magnet, or both.

There are several microchip-based magnetic sensing technologies that could be used in biosensors including Hall effect, anisotropic magnetoresistance (AMR), Giant Magnetoresistance (GMR), and Magnetic Tunnel Junctions (MTJ). This disclosure focuses on GMR but is not meant to exclude the use of the others, which may have relative advantages in certain cases. A GMR detector is a multilayer metal film whose total thickness is in the range of 10 to 100 nm. Resistors are formed from the film using standard semiconductor wafer processing techniques such as photolithographic patterning and ion mill etching. Patterned resistors are about 1 micron wide, and arbitrarily long. The total resistance of a typical GMR resistor is about 10 ohms times the length:width ratio. For example, a 2 micron×100 micron resistor has a nominal resistance of (100 microns/2 microns)*10 ohms per square=500 ohms. By design, the GMR sensor is sensitive primarily along one axis in 3 dimensional space. This direction is usually in the plane of the film, but can be either parallel or perpendicular to the long dimension of the resistor. The electrical resistance of the GMR sensor is used in a circuit to infer the magnitude of the total magnetic field at the sensor location. A constant current is passed through the resistor, the voltage measured; the resistance is the voltage/current. This voltage is independent of the frequency of measurement, and exists at "DC."

The $H_{label}$ has the shape of a "dipole" field, much like the magnetic field of the Earth. Its magnitude drops off as the function $(r/d)_3$, where d is the distance from the label and r is the label radius. Also, the field from the label is not uniform in the plane of the sensor. Clearly, the magnetic field effect of the label is greatest in the region immediately beneath it, and decreases rapidly as one moves out from underneath it. So the sensor resistance only changes appreciably in that region. Ignoring, for a moment, the non-uniformity of $H_{label}$, one can see the effect of the label on magnetic fields detected by the sensor. Referring to FIG. 2, one can see that for some $H_{applied}$, there is an $H_{label}$ in the opposite direction that decreases the total field at the sensor. This effect is measured as a voltage change by electronic instrumentation.

If the label is much smaller than the total size of the sensor, the total fractional resistance change will be much smaller than if the label was the same size or larger than the sensor. In fact, the total resistance change it is roughly proportional to the fraction of the sensor area that the label covers. This is a very useful feature for measuring more than one label.

Label Layers.

In most bioanalytical applications, detecting a single label is not useful. Rather, it is necessary to measure, within the detection region, the surface density of labels in a quantitative way so that the concentration of some analyte can be inferred. A drawing of a sensor with more than one label above it is shown in FIG. 3. Notice that the sensor area can be extended almost arbitrarily by patterning it in a "serpentine" shape. Also, it is possible to create large arrays of very small sensors, which have both high precision and large area. Assay conditions must be set to match the analyte concentration range of interest, so that after the time interval of conjugation and labeling, the number of bound labels is somewhere between zero and full coverage. The total resistance change of the sensor then corresponds to the number of labels bound there.

Some early examples of this arrangement were demonstrated using GMR sensors under a 200 micron diameter circular spot to detect 2.8 Dynal labels bound to the sensor through a specific binding of captured DNA [Baselt U.S. Pat. No. 5,981,297]. The dynamic range of the detector was from 10 labels to about 5000 labels, nearly 3 orders of magnitude. This level of label detection corresponded to a maximum concentration of 100 fmolar DNA as measured using optical detection. An analogous result was obtained using ~60 nm diameter labels in order to quantify the immunological interaction between surface-bound mouse IgG and α-mouse IgG coated on superparamagnetic labels.

Spots and Plugs.

Three-dimensional sample volumes are, of course, important in bioanalysis. It is possible to use GMR technology to measure the magnetic content of very small volume like those in a microfluidic channel or lateral flow membrane. Detecting a magnetic plug or volume works the same way as a single label, or layer of labels, in that the sensor detects changes in the local magnetic field due to the presence of magnetic material there. The complicating fact is that not all of the magnetic material can be said to be at the same distance from the sensor (recall: the stray magnetic field from a label goes as $(r/d)_3$). The fact that the math is more complicated does not mean that the detector won't work; rather, that more care is required in sensor calibration and data analysis.

Magnetic Labels in Lateral Flow Strips.

A complete system for detecting magnetic labels in lateral flow strips has been developed and is being marketed by MagnaBioSciences. Descriptions of their system have been published [RT LaBorde and B O'Farrell, "Paramagnetic Particle Detection in Lateral-Flow Assays," *IVD Technology* 8, no. 3 (2002): 36-41. B O'Farrell and J Bauer, "Developing highly sensitive, more reproducible lateral-flow assays Part 2: New challenges with new approaches", *IVD Technology* 12, no. 6 (2006): 67. U.S. Pat. Nos. 6,046,585, 6,607,922]

This system has been used successfully for very quantitative work on e-coli according to the manufacturers, out-performing two reference systems for the application. The physics of detection is different for the MagnaBioSciences system than for the GMR system. The magnetic labels are paramagnetic, just as are discussed above. But the detectors are loops of wire, or inductors. The voltage induced in a loop of wire is proportional to its area, the frequency and magnitude of the oscillating magnetic applied field. There is no detected signal in a loop or coil if the field does not change in time. The bioanalytical volume being measured in this case is on the order of 1 mm×3 mm×0.4 mm. The first dimension is the width of the capture stripe on the strip; the second and third dimensions are the strip width and thickness, respectively. The pickup coils for this system must be well matched to the sample dimensions.

Most of the early demonstrations using GMR in bioanalytical applications assumed that the sample handling would be done in a lab-on-a-chip type device. Here, the passive wicking action of lateral flow strips is replaced by active pumping and/or vacuum. Well defined reservoirs and microfluidic channels replace the spots and strips. Consequently, labs-on-a-chip have the ability to perform a greater variety of functions, and do them much more precisely, but at the expense of greater product complexity.

Ferrofluid plugs of magnetic nanolabels (aqueous suspension of 10 nm magnetite labels, Ferrotec EMG 507) diluted to 1.2% v/v magnetite with a Tris-buffered fluorescein solution (3 mM after mixing, pH 8.0) for fluorescence imaging) were detected by a GMR sensor beneath a microfluidic flow channel. The plug dimensions were 13 microns×18 microns×85 microns for a total volume of 20±3 pL and contains about $5 \times 10_8$ 10 nm labels. The first two dimensions are the channel width and depth, respectively, while the third is the plug length. The individual labels are many times further away from the sensor than their diameter. While this is not entirely analogous to the lateral flow strip example, it does show that the GMR sensor is capable of detecting and analyzing "composite plugs" nearby in contrast to counting single labels.

Microchip-Based Magnetic Sorting and Concentration.

Most magnetic labels are designed and used primarily for capturing and concentrating analytes. So it is natural to adapt macro-scale magnetic force systems to miniature bioanalytical systems. Electrical current passing through a wire generates magnetic fields that are directed around that wire. This means that wires on a circuit chip generate magnetic fields that impinge upon the magnetic label on the chip or nearby. When combined with other field sources, such onchip wires can be used to magnetize labels and attract or repel them. The magnetic forces are sufficient to enable the sorting of magnetic objects in flow streams [Tondra, et. al. "Design of Integrated Microfluidic Device for Sorting Magnetic Beads in Biological Assays," *IEEE Transactions on Magnetics*, 37, no. 4 (2004): 2621-2623. N Pekas, et. al, "Magnetic particle diverter in an integrated microfluidic format;" Journal of Magnetism and Magnetic Materials, 293, (2005): 584. U.S. Pat. No. 6,736,978, Porter et al.; U.S. Pat. No. 6,875,621, Tondra]. These patents are incorporated herein by reference. Combining the ability to direct magnetic labels in flow along with a means to detect them downstream presents the opportunity to count magnetically labeled analytes as they flow by.

Cell sorting and detection has been demonstrated using this technique. Since single labels can be detected in flow, it is possible to make ultra-miniature flow detection systems for molecular analysis using magnetic label-carriers. For additional background, see the excellent review articles on magnetoresistive-based sensing [DL Graham, H A Ferreira and P P Freitas, "Magnetoresistive-based biosensors and biochips," *Trends in Biotechnology* 22 (2004): 455-462] and microscale sorting [D L Graham, H A Ferreira and P P Freitas, "Magnetoresistive-based biosensors and biochips," *Trends in Biotechnology* 22 (2004): 455-462].

Magnetic concentration in a flow strip device is described in U.S. Pat. No. 6,136,549, Feistel, but the detection means in that patent is optical, not magnetic. Details of flow permeable membranes as they are used with optical detection are described in U.S. Pat. No. 7,141,212, Catt, describes flow membranes, systems for optical reading. Electronic reading of fluorescently labeled assays is described in U.S. Pat. No. 5,837,546 by Allen.

SUMMARY OF THE INVENTION

It is often desirable to have many assays (multiplexed) performed in the same device, saving time and money. In an In-Vitro Diagnostic device, this means breaking up the single "test" and "control" bars across the strip into several discrete spots. Lateral flow strip technology appears to be ready to support multi-spot arrays, but there are no disposable multiplexed assays on the market.

Integrated microchip based sensors have been configured to detect and quantify a wide range of bioassay labels, ranging from single label detection to plugs containing millions of labels. These sensors, along with integrated magnetic means for manipulation, have the potential to impact several aspects of in-vitro diagnostics. Many of the results reported in the literature to date have been demonstrated as part of a microfluidic lab-on-a-chip type system. However, the complexity of lab-on-a-chip systems, along with the immaturity of the manufacturing capabilities for them, has slowed their commercialization. Lateral flow strip technology, in contrast, has a well established commercial infrastructure and manufacturing base.

Also, non-integrated electromagnetic effect field detectors have been demonstrated for membrane-based assay devices using electromagnetic effect field labels. There are no examples of integrating electromagnetic effect field microchips into membrane-based assay devices.

Thus, integrating microchip technology directly into flow membrane technology is a novel invention that can provide a faster route to combining electronics with in-vitro diagnostics. The very low cost per sensor, in high volumes, enables disposable sensor electronics.

The term integrated sensor, in this disclosure means the detector is permanently combined with the flow structure, and is designed to be discarded or stored with the flow structure once the assay has been completed. This is distinct from an non-integrated sensor, which is not consumed with each assay; rather it remains in place to collect data from more assay structures.

There are several advantages of integrated electromagnetic effect field detectors. The main one is vastly improved sensitivity and precision for measuring the location and amount of electromagnetic effect field labels in a given location in an assay membrane. As the size of spots shrinks, and their areal density increases, it becomes increasingly difficult (if not impossible) for a single large detector far away to resolve signals from an array of tiny spots. The challenges that must be addressed in order to bring integrated electromagnetic effect field detectors to market are related to the lack of a design for such a thing, and a lack of established manufacturing capability for both the microchip and assay flow structures. The invention in this disclosure addresses these challenges with novel structures and assembly procedures that result in an integrated microchip electromagnetic effect field detector that can be manufactured in a cost-effective way.

The present invention provides an integrated detection system for membrane-based disposable assay cartridges. The system uses disposable assay structures whose fluid sample handling is based on flow permeable membranes. Bibulous paper membranes are one kind of flow permeable membrane. Nitrocellulose, fiberglass, and nylon are two commonly used materials for flow permeable membranes. These membranes perform several functions including: providing a flow path through an otherwise solid structure, providing a solid matrix for depositing chemical reaction materials, acting as a filter for relatively large objects in the flow. Ideally the membrane has regular pore size, controlled and uniform flow rates, and well controlled surface chemistry of the solid matrix.

The detectors for the system are integrated into the disposable assay cartridges. The assay devices are constructed so that a tiny sensor chip is mechanically connected to one of the outer boundaries of the flow membrane with an adhesive or other bonding mechanism. The sensor chip area is orders of magnitude smaller than the area of the flow membrane, which enables cost effective use of both high precision components and low cost membranes in the same device. In one embodiment, the membrane has micropatterned features that divide it into many parallel lanes. In another embodiment, there is a chip-scale membrane in addition to the macro-scale membrane. In all cases, the system provides for proper positioning and angular alignment of the detector chip with the externally provided electromagnetic effect field source. Also, there are features for aligning the analyte spots with the integrated sensors. The system provides for electrical connections from a permanent reader device to the disposable assay cartridges. It also provides for analog voltage signal conditioning, analog-to-digital conversion and data processing.

Planar integrated circuits are commonly known in the field of semiconductor electronics as "integrated circuits". They are most frequently produced on a semiconductor substrate using sequences of thin film whole-substrate manufacturing steps including: controlled deposition of thin layers of additive material, and selective removal of portions of said thin layers of additive material; selective thin layer impurity implantation. "Whole substrate" means that the entire substrate is subjected to the coating or removal process, rather than a small portion or single spot. In contradistinction, an ink jet print head adds material to a tiny spot on a paper substrate, and a drill bit removes material at only one location of a substrate at a time.

Some planar integrated circuits are produced on rigid insulating substrates such as glass or titanium oxide, which are chosen for optical clarity, or mechanical toughness, respectively.

Other planar integrated circuits are produced on flexible plastic or polymer substrates. These have some interesting advantages in that they can be used in roll-to-roll production processes, unlike rigid semiconductor wafers. However, it is not always possible to obtain epitaxial crystal growth on a polymer substrate.

Overall an electromagnetic effect sensor substrate must perform, or be compatible with, the following functions: providing adequate electrical isolation from (or connection to) other surrounding material, providing a benign exposed surface for construction of the sensor that is to be supported on it, enabling manual or automated handling of the substrate during the fabrication process, providing an exposed surface for good adhesion between the substrate and the sensor it supports, providing mechanical integrity to the supported structures, and having adequate properties regarding thermal expansion and heat conductivity over the intended range of manufacturing and operating temperatures.

Generally, the deposited thin layers have a thickness less than 1,000 times their length and width, as deposited. For example, the thickness of an aluminum layer for the formation of conductive structures deposited on a 100 mm diameter substrate is about 0.001 mm (1 micrometer=1 micron). Of course, the aspect ratio (thickness:width) of aluminum conductive structures after selective removal can be any value. A typical planar integrated circuit wire has an aspect ratio of 2:1. For example, a 0.5 micron thick film could be patterned into wires that are 1.0 microns wide, and of arbitrary length and shape. This patterning is achieved using photolithographic masks whereby a thin film light-sensitive polymer is spun onto the substrate, the polymer is exposed to light shone through a mask, said mask having dark regions where the material is supposed to stay and clear regions where it is supposed to be removed. The light hitting the light-sensitive polymer causes it to become substantially weakened so that the exposed portion can be rinsed away in specific solvent while the unexposed portion remains.

Because planar integrated circuits involve integration of multiple layers, and selective addition and removal of some layers, the resulting structures are not necessarily flat; almost certainly not on an atomic or molecular scale. Rather, they can have steps, holes, and other three dimensional features. The word "planar" here refers generally to the methods and scale of their manufacture, not to the resulting device surfaces.

A planar integrated electromagnetic effect field sensor is defined as an electromagnetic effect field sensor that is made as a planar integrated circuit. These sensors are sometimes provided as a "chip". Such chips are created by sawing the sensor substrate into many separate pieces after the integrated circuit fabrication process.

BRIEF DESCRIPTION OF THE DRAWINGS

FIG. 3. Perspective view of a GMR sensor (thin serpentine) with some paramagnetic labels immobilized on top. The plain sensor chip surface (diagonal hatch) has been modified in a region above the sensor (cross-hatch) to capture labels. Wires connect to the GMR sensor from beneath and run off the page to external circuitry.

FIG. 4. Cross section view of the lateral flow assay with integrated detectors.

DETAILED DESCRIPTION

Figure 1A:
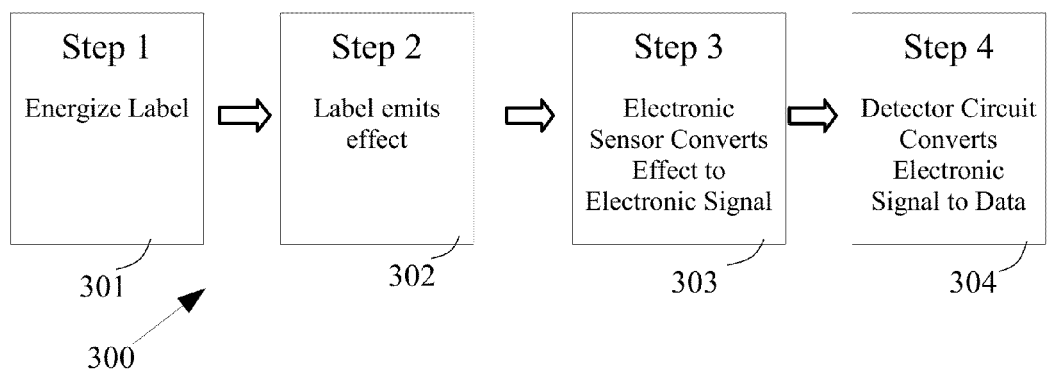
FIG. 1A. A step-by-step diagram showing the sequence of events involved in using an electronic sensor to detect a label and generate electronic data FIG. 1B. A block diagram of the components required for electronic detection of a label, and the interrelationships between the components.
Figure 1B:
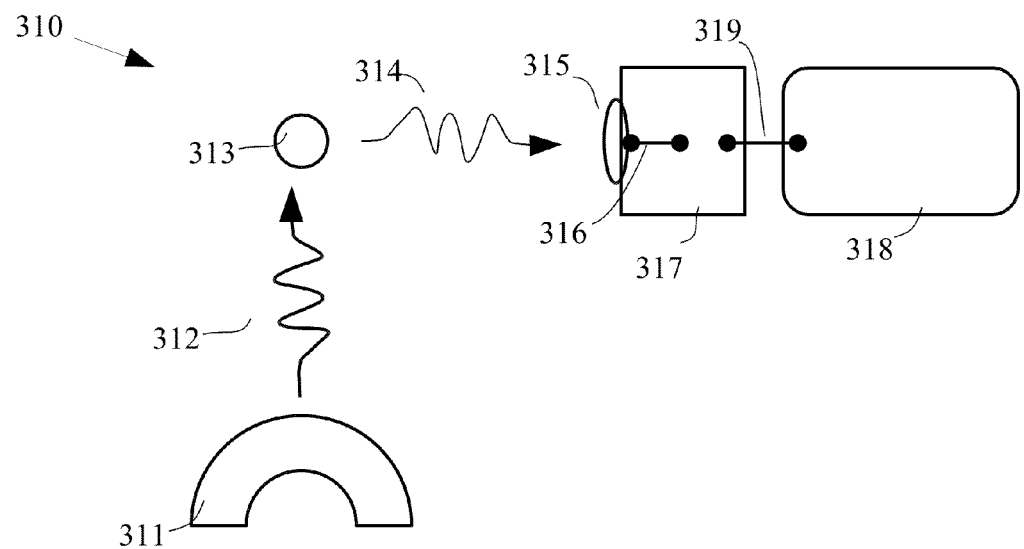
FIG. 1C. A single magnetic label bound to the sensor chip surface, as in an immunoassay.
Figure 1C:
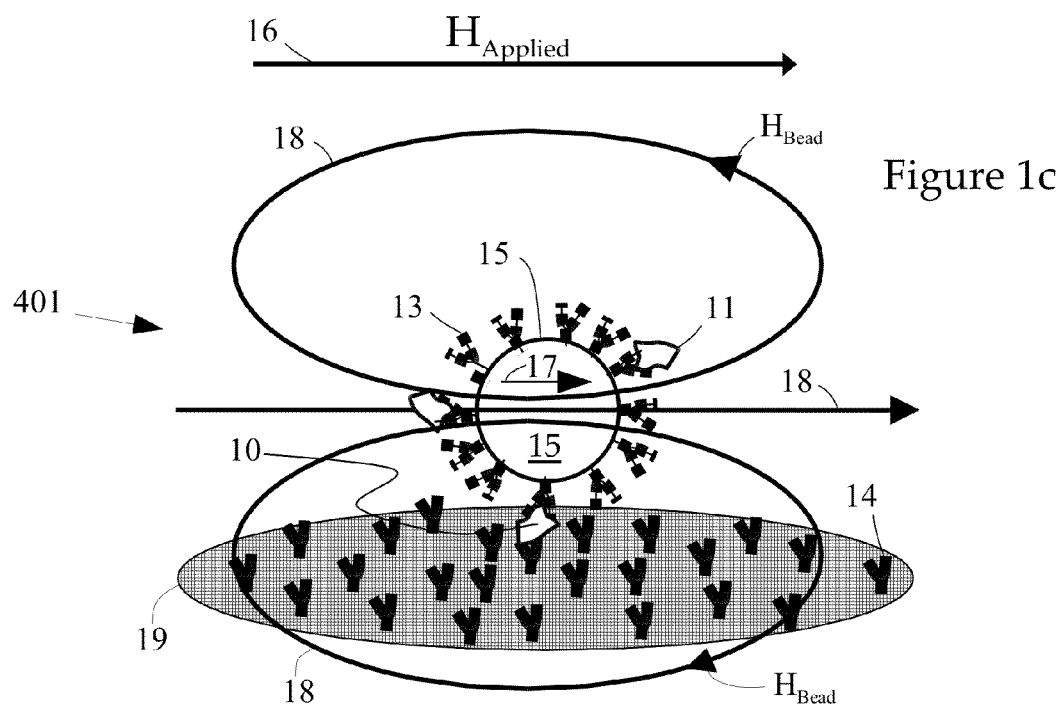

The purpose of the invention is to measure the quantity of bioanalyical material (analyte) in a given sample. An immunoassay is a common form of bioassay where the analyte is captured by antibodies. FIG. 1 shows an analyte molecule 10 "sandwiched" between: one of the many capture antibodies, 14, on the sensor surface 19; and one of many "probe" antibodies, 13, on a paramagnetic label 15. Label 15 also has other antibodies, 11, captured on it, but not sandwiched. An applied magnetic field ($H_{Applied}$), whose orientation is indicated by vector arrow 16, induces a linear increase in the magnitude of magnetization, M, in label 15. The orientation of M is indicated by vector arrow 17, it is always parallel to $H_{Applied}$.

A Giant Magnetoresistive (GMR) detector 19 measures the total magnetic field along its axis of sensitivity which is the sum of $H_{Applied}$ and $H_{label}$, whose orientation in the region around the label is represented roughly by oval curves 18.

Figure 2:
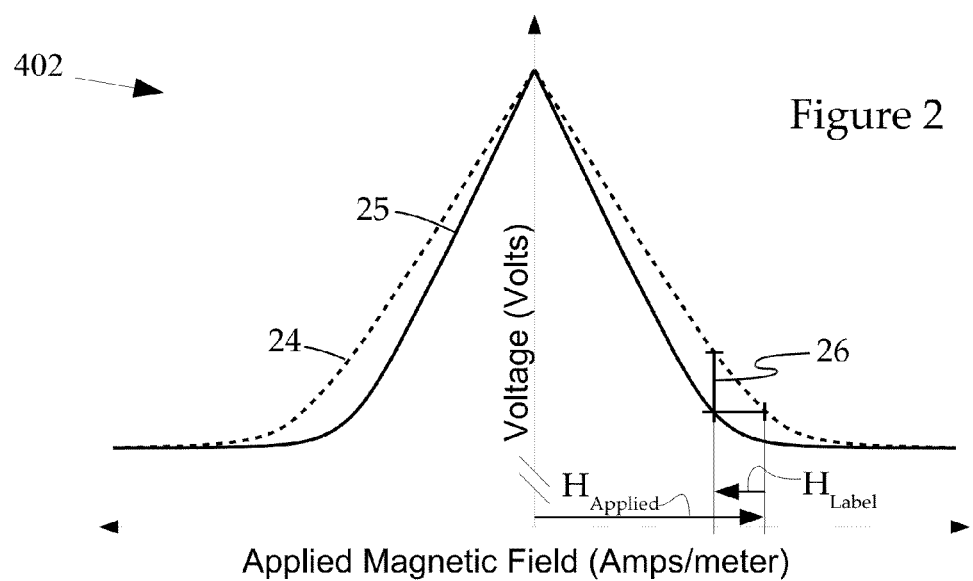
FIG. 2. Voltage vs. $H_{applied}$ of a GMR sensor with and without a label on it. The units are somewhat arbitrary, but the shape of the curve is representative.

A commonly used form of GMR has the resistance vs. $H_{Applied}$ shown in FIG. 2. The vertical axis is called "Volts", which is what one measures using a voltmeter when passing a constant electrical current through the device. The lower curve 25 represents the ordinary result, while curve 24 is the result when a label is present on top of the sensor. The difference between them is the measured signal 26.

A perspective view of a GMR sensor is shown in FIG. 3. Thin film GMR material is patterned into long narrow stripes whose width is usually on the order of 1 micron. The length is arbitrary. A GMR sensor 30 has been patterned into a "serpentine" shape in order to cover a larger area with a single sensor. Electrical interconnection to the sensor is provided by buried left and right metal leads 31 and 32, made of Cu. Fabrication techniques for these leads and sensors is described in detail in U.S. Pat. No. 6,875,621, which is herein incorporated by reference. A region of the plain insulating chip surface 33 has been modified in the region 34 above the sensor 30 to cause labels 35 to be specifically bound by a biochemical binding event such as in the manner shown in FIG. 1. The sensor infers the quantity of bound bioanalyte by measuring the magnitude of $H_{label}$.

A side view of one embodiment of a disposable assay cartridge is shown in FIG. 4. A liquid sample 40 is introduced at the top surface of the flow permeable membrane 41, which may act as a filter and/or have sample chemistry bound within. The general flow of the sample follows the heavy dotted line 60. This flow is essentially a wicking action that continues until wicking pad 45 is full. The sample flows through pad 42 where electromagnetic effect labels, 44, coated with label conjugates (antibodies) are picked up by the analyte as it passes through. These electromagnetic effect labels are generally of diameter a few hundred nanometers. If they were too much bigger, say about 10 microns, they would plug up the open spaces in flow permeable membrane 43.

A lane of electromagnetic effect field sensors is shown with 6 sensors 51, 52, 53, 54, 55, and 56. They are situated on the top surface of integrated sensor chip 80 in sequential order in the direction of flow. Each of these sensors has a label detection zone 50 in the portion of the flow permeable membrane 43 to which they are adjacent. These zones are not defined by actual material edges or boundaries. Rather, they are defined as the three dimensional region in membrane 43 near a given sensor in which labels can be detected by that sensor, should the labels be therein.

Nitrocellulose and other membrane materials used for flow permeable membrane 43 is often provided on a flexible backing material to add strength to the membrane and make it more easily handled. A key part of the present invention is the incorporation of integrated electromagnetic effect field sensor chip 80, and other integrated circuit chips, into backing structure, 46. The backing structure should be thin, insulating, and durable. Polyimide, Mylar, and Capton are names for commonly used materials.

Electromagnetic effect field sensors 52 and 54 on sensor chip 80 are adjacent to label capture sites 57 and 58 in membrane 43. These sites are enable the performance of an immobilization "sandwich assay" as described in FIGS. 1 and 3. Electromagnetic effect field sensors 51 and 53 are reference sensors. These provide for simpler electronic compensation schemes in balancing and calibrating the detection system. Alternatively, they could also be used beneath capture regions for a denser array. Electromagnetic effect field sensor 56 is immediately beneath the "control" capture site, while electromagnetic effect field sensor 55 is a reference sensor for the control line. Low cost interconnection circuitry 48 is provided on the backing structure 46 to take sensor signals to a control system. This is done through electrically exposed contact points 47, shown here on the bottom side to match the system design shown later. Overall in FIG. 4, the membrane portions are established art. The new inventions are in the backing and how it is combined with the rest of the system.

During manufacture, spots or stripes of the capture ligand (antibodies) are placed, at capture sites 57 and 58, and a universal capture agent is placed at the "control" site 59. Label capture sites 57 and 58 may be measuring for two different analytes, or they may be set up to allow measuring a larger dynamic range of concentrations for a single analyte.

Figure 5:
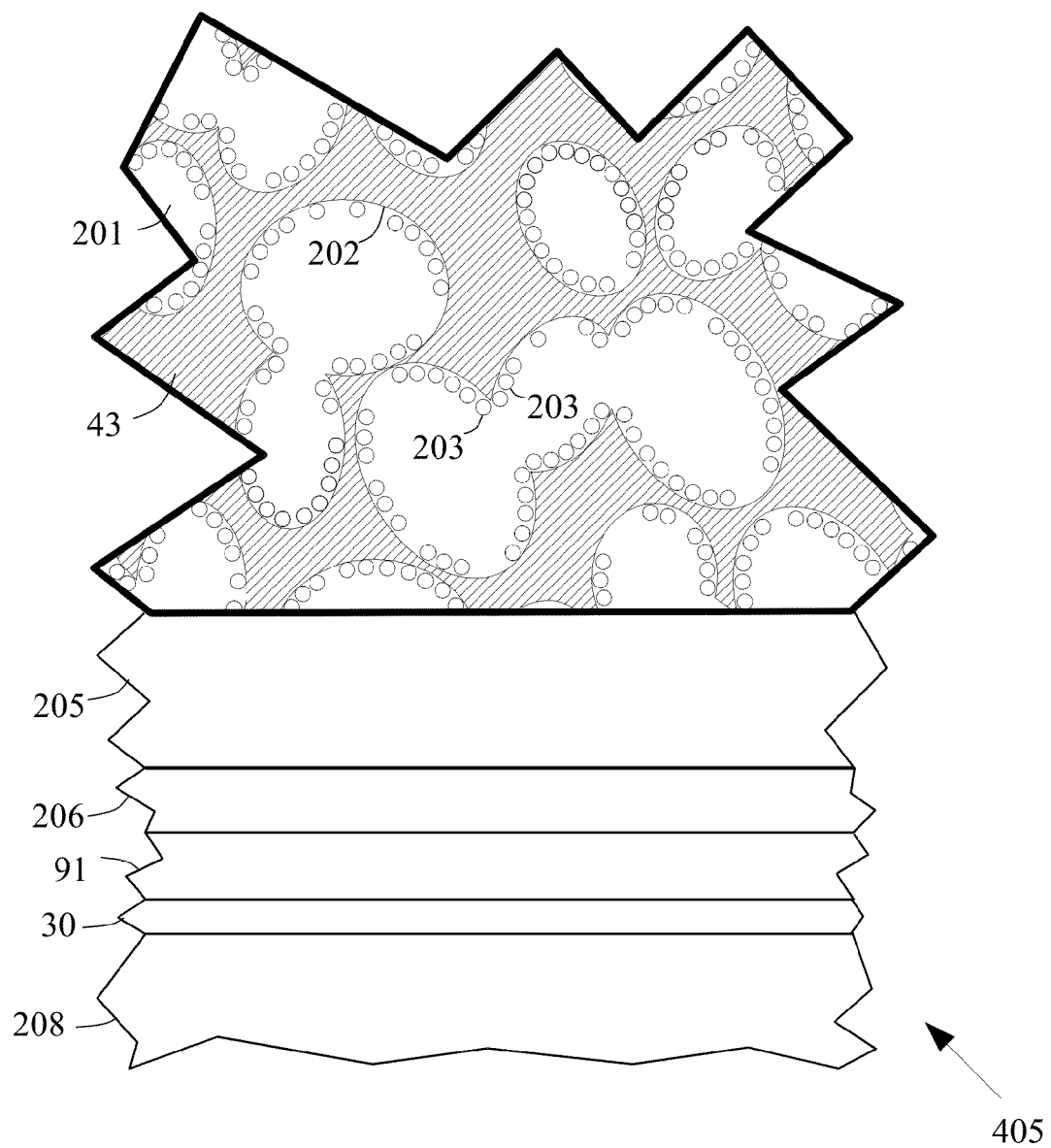
FIG. 5. Cross section close view of sensor chip, membrane, immobilized labels, label detection zones, and material layers.

A close-up section view of flow membrane 43 is shown in FIG. 5. It has hollow pores 201 that allow fluid to pass through (A continuous path is not shown in this section view, but must exist somewhere in the membrane for it to work) and provides a very large surface area for chemical binding of labels. This view is from within a label capture site 57 so the surfaces are coated with capture antibodies 14 (too small to be shown, but see FIG. 1*c* for a view of these). Magnetic nanolabels 203 are bound to biochemically prepared surface 202 when analyte 10 is sandwiched between the label and surface (also as in FIG. 1). Some other layered structures are shown. Layer 205 is an adhesive, about 1 micron thick, that binds the membrane to the integrated sensor chip. The chips surface is electrically passivated with a 0.1 micron thick conformal coating of polyimide 206. During fabrication, GMR sensor material 30 is deposited on sensor chip substrate passivation 208, a nitride or oxide of silicon. The underlying silicon wafer is not shown. Once the sensors 30 are patterned, they are electrically passivated with a thin layer of silicon nitride, 91. Together, these structures provide an electrically robust but very thin barrier between GMR sensor 30, which should be electrically isolated to function properly, and the fluid running through pores 201 in flow membrane 43.

Figure 6A:
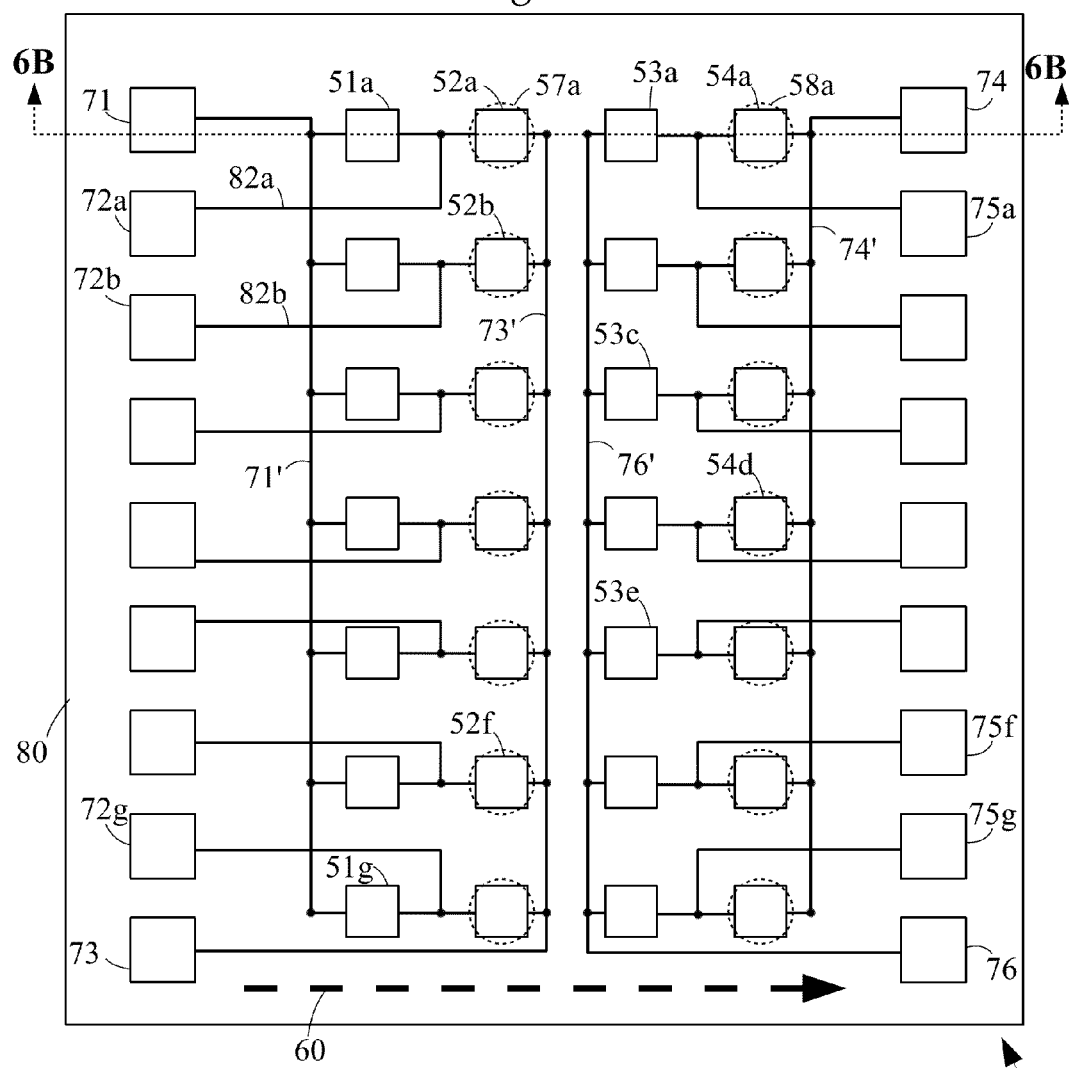
FIG. 6A. Plan view of the integrated detector chip.

A plan view of electromagnetic effect field sensor array chip 80 is shown in FIG. 6A. The electromagnetic effect field sensors are squares marked 51*a*, 52*a*, . . . 51*g*, etc. There are a total of 28 sensors in this 4×7 array. The numbers 51, 52, 53, 54, correspond to the sensors shown from the side in FIG. 4. The numbers 57*a* and 58*a* refer to dashed circular regions that correspond to the label capture sites 57 and 58 in FIG. 4. The size of electromagnetic effect field sensor chip 80 is about 1 mm×1 mm, and the sensors are about 80 microns across. In this plan view, one can see that there are 7 "lanes" of sensors, indicated as "a" through "g". Since the flow is from left to right as shown by dashed arrow 60, there are 7 parallel lanes in the flow path that pass over the sensor chip. Many layers of material have been omitted from this view in order to describe the chip construction carefully.

The ideal detector size for an array designed to measure analyte concentration through specific binding of labels to label capture sites is to have the sensor size match the label capture site spot size, and be as close as possible to the spots. The spots need to be situated so that the electromagnetic effect field signature from labels captured at one capture site is detected primarily by the proper sensor. Supposing the flow membrane 43 has a thickness of about 100 microns, the spot size could be about 80 microns in diameter, and spaced at 200 microns, center to-center. It should be noted that the method of creating analyte capture spots on the membrane has limits to its precision in terms of spot size and spot location.

Buried metal interconnections are indicated by solid lines running from the sensors to the large square contact pads at the side of the chip. Upper left pad 71 and lower left pad 73 provide power and ground via their respective bus bars 71' and 73' to the 7 pairs of sensors 51*a* to 52*a* through 51*g* to 52*g*. The sensor signal is taken out to pads 72*a* to 72*g*. Similar wiring is provided on the right half of the chip. Clearly, the wire routing between sensors and pads is drawn schematically, and is meant to convey electrical connectivity, not a geometrically precise drawing.

Figure 6B:
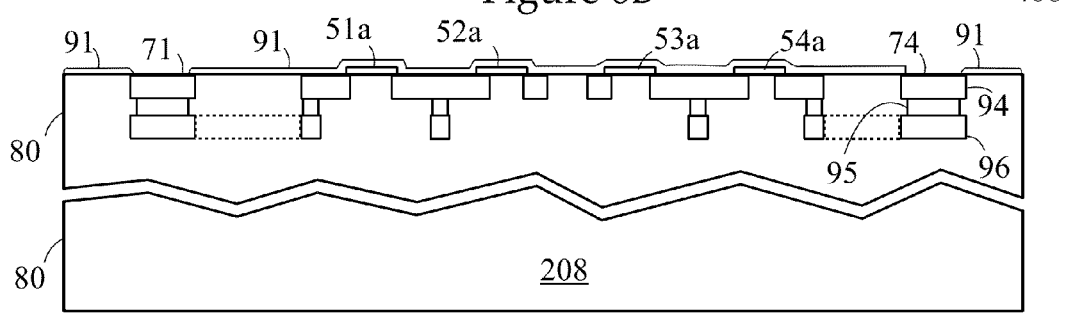
FIG. 6B. Cross section view of the integrated detector chip.

A section view taken along the line from upper left pad 71 to upper right pad 74, and passing along the "a" row of sensors, is shown in FIG. 6B. Two layers of metal interconnection shown as 94 and 96 are formed on sensor chip 80 to a thickness of about 1 micron using what is known as the "copper damascene process". There are also vias and plugs 95 for making vertical connections between the layers. The thin silicon nitride passivation layer 91 is shown. Note that it is open to the outside only above the upper left and upper right pads 71 and 74, thus electrically covering sensor elements 51*a*, 52*a*, 53*a*, and 54*a*.

Figure 7A:
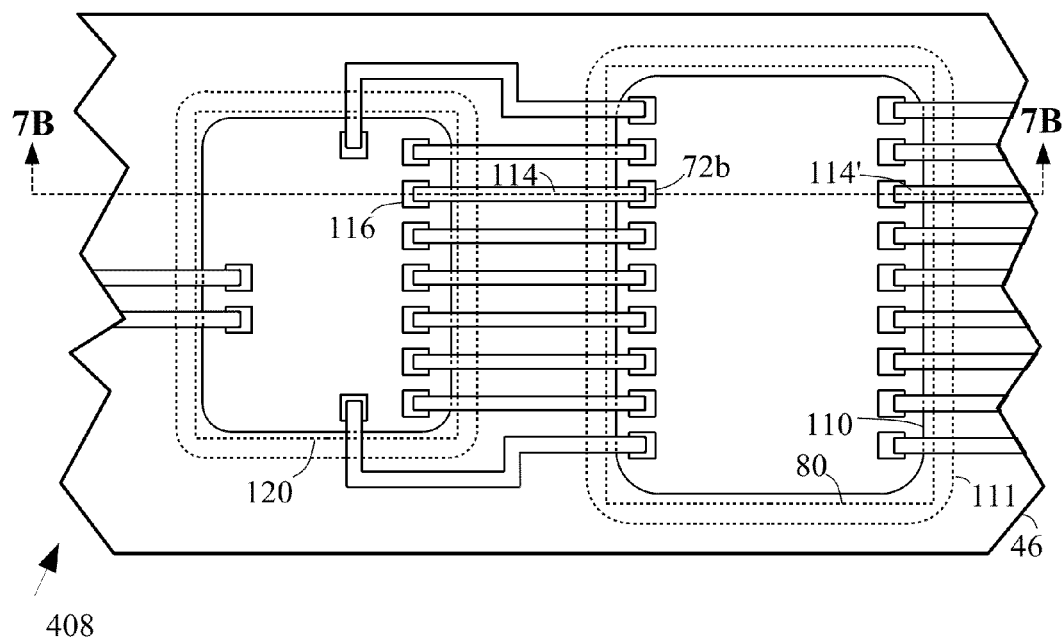
FIG. 7A. Plan view of integrated detector chip connected to signal processing chip on membrane support.

A plan view of the central region of flow strip 43 is shown in FIG. 7A. The details on electromagnetic effect field sensor chip 80 have been removed, leaving only the bonding pads at the chip periphery. A second semiconductor-based chip 120 is shown at the left. It does not necessarily have any sensors, but performs important functions such as analog signal amplification, supplying conditioned power, and multiplexing the output so fewer wires are needed going to the outside world. Other non-sensing functions that can be performed by the integrated chips include magnetic guiding and attracting using both passive and active integrated magnets. Electrostatic forces can also be applied. And other sensor types like capacitive and optical can be integrated using the same basic process. These chips are connected to each other and the external system though another layer of wires that is formed through an additive process (for example, ink jet printing). These wires include 114, which connects bonding pad 72*b* to bonding pad 116, and 114', which runs off to another chip not shown.

Figure 7B:
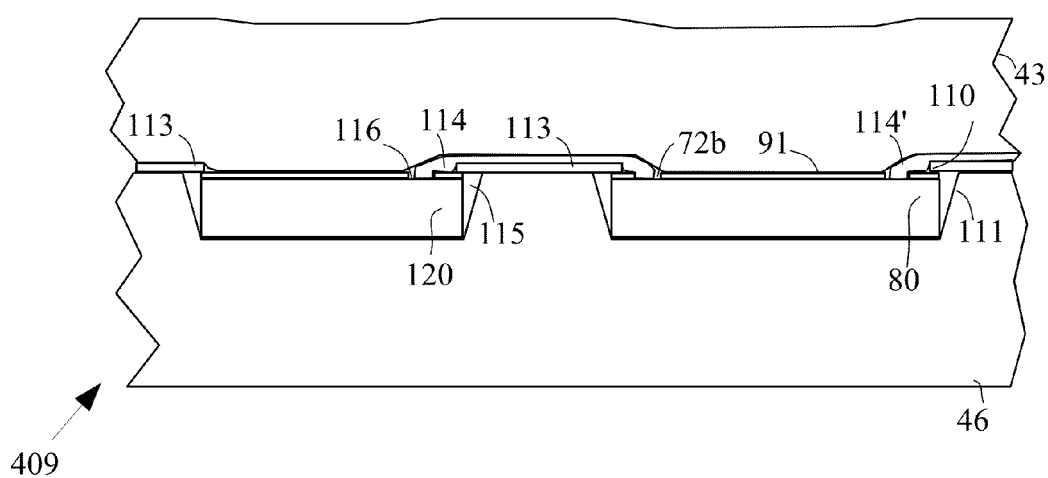
FIG. 7B. Cross section view of integrated detector chip connected to signal processing chip on membrane support.

An important innovation shown here is the very thin patterned insulating membrane 113. This plastic layer forms a "bridge" across the gaps 115 shown in FIG. 7B (section view). In order for the flow membrane to work properly and be close enough to the detector chip for accurate detection, the supporting surface should be relatively flat. This is why indentations 111 are formed in backing structure 46 so that the top surface of sensor chip 80 is "flush" with the top surface of 46. However, there is never a perfect fit between the chip and the backing structure. Wire bonds would work for this problem except that they stick up above the chip surface by a few hundred microns. The device shown here maintains good electrical connectivity with a flat surface. Conductors 114 and 114' pass over the thin membrane 113 on their way between the holes in dielectric insulating layer 91 leading to bond pads 116 and 72*b*. Because of the very low profile, membrane 43 is in direct contact with insulating layer 91, though the polyimide and adhesive layers are there, but are left out for the sake of clarity.

Figure 8A:
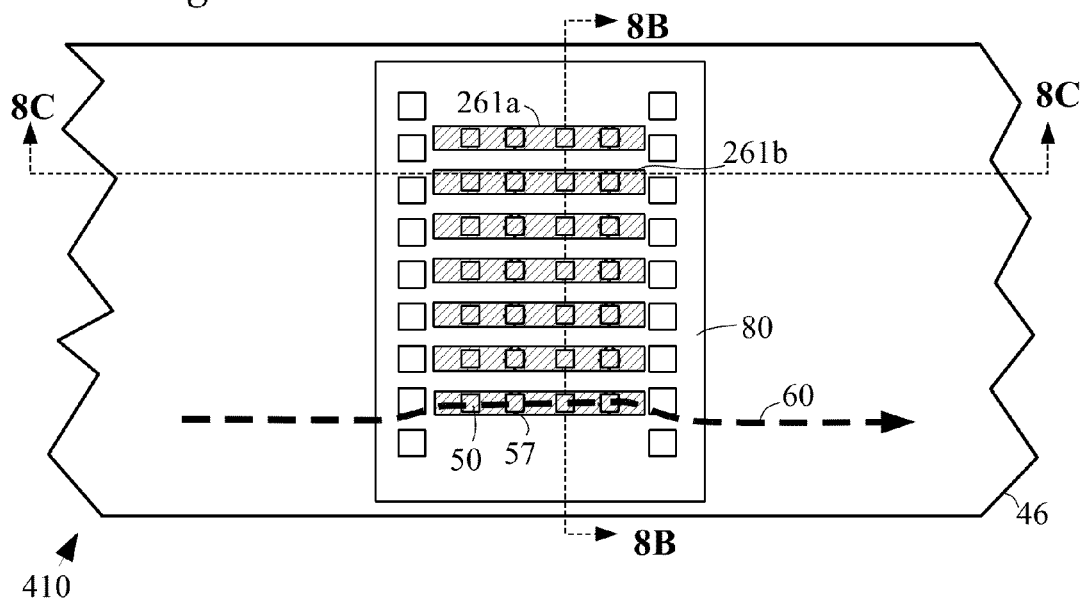
FIG. 8A. Plan view of integrated detector chip with micro-patterned permeable membrane material on top.

A plan view of another embodiment of the invention is shown in FIG. 8A. Electromagnetic effect field sensor chip 80 is still sitting in indentations or holes in backing structure 46. But some additional flow permeable membrane material has been integrated onto the chip during its wafer manufacturing process. Through photopatterning and/or sawing, the on-chip membranes flow diversion features are formed so the flow path 60 has 7 parallel lanes 261*a*, 261*b*, etc., that pass directly over the sensor rows. The sample is forced to flow, along flow path 60, more in regions close to the sensors, and potential for chemical cross-talk is reduced.

Figure 8B:
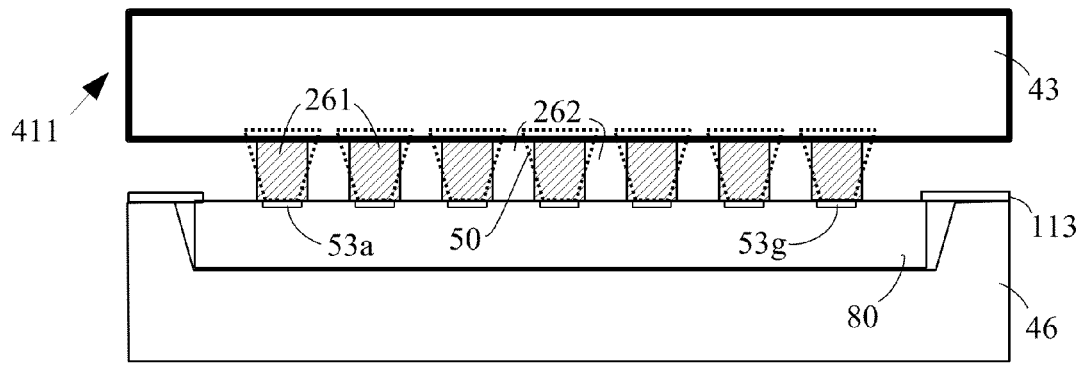
FIGS. 8B, 8C. Cross-section view of integrated detector chip with micro-patterned permeable membrane material on top.
Figure 8C:
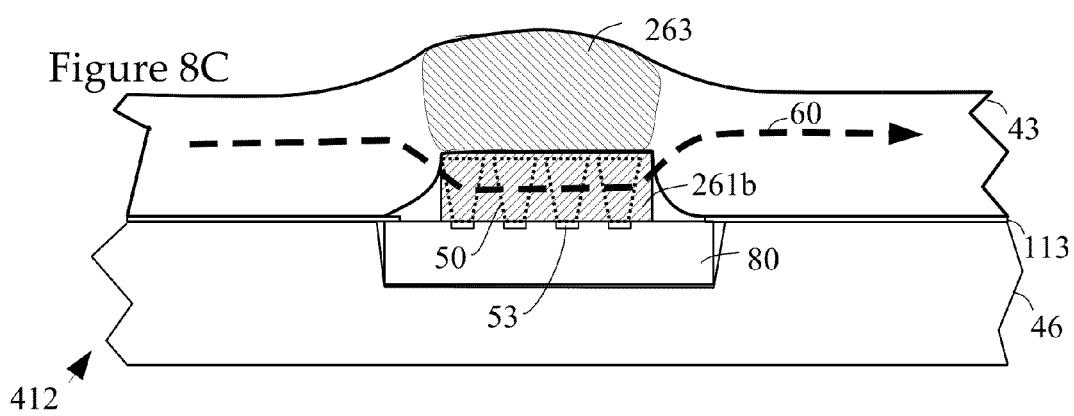

A section view of this structure is shown in FIG. 8B. Here one can see the 7 membrane lanes, 261, directly above the sensors. Also, there are non-flowing regions, 262. These regions are formed through lithographic processes that can deposit "plugging" material in regions 262. Or the membrane material can simply be removed. The other section view for this drawing is shown in FIG. 8C. Here is shown a plug, 263, intentionally formed in main membrane 43 in order to divert the flow to be as indicated by dashed arrow 60.

Figure 9:
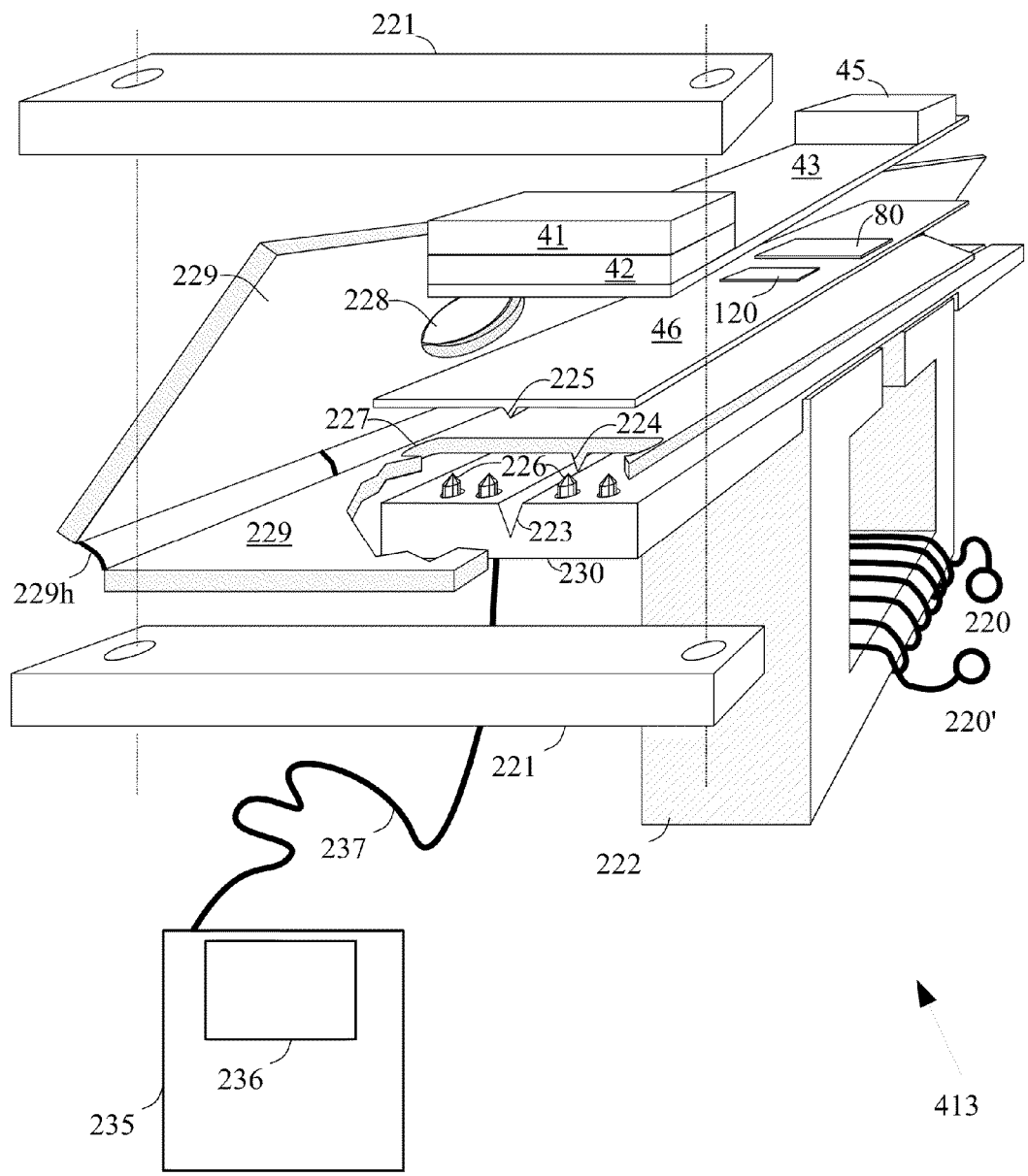
FIG. 9. Perspective view of reader system including magnetic field source, reader support electronics, assay case, and flow membranes.

One embodiment of the sensing system is shown in FIG. 9. This is an "exploded" view so the surfaces of various components are visible. A miniature magnetic field source is made of magnetic yoke, 222, which has some windings that connect to control circuitry via connections 220 and 220'. The gap in the yoke is where the usable field is generated. There is also usable field just outside the gap, which is the configuration shown here. A mechanical positioning plate, 230, is situated firmly with respect to magnetic yoke 222 so that the position of disposable sensors is well known during the reading period. Positioning plate 230 is also fitted with electrical contacts, 226, designed to easily make and break connections to disposable sensors. The disposable membrane backing structure, 46, has a means for mechanical alignment with respect to the yoke. Here is shown a "V" extension, 225, that fits into a matching notch, 223, of positioning plate 230. A similar "V" extension, 224, is provided on the bottom side of the plastic assay case, 229. The bottom of the case has a hole, 227, that enables the external electrical connections to connections 47 on the bottom side of membrane backing structure 46 (see FIG. 4). The top side of assay case, 229', has a hole for inserting sample. Top 229' and bottom 229 of the assay case are connected with hinge 229$h$.

A means of securing the disposable assay cartridge to the reader system are provided in the form of clamps 221, 221'. Assay control system 235 with graphical user interface 236 is connected electrically with the reader hardware interface via cord 237.

The result of this design is a very low power magnetic field source because it is so small. The disposable magnetic assay cartridges are put into position, read electronically, and then removed or discarded.

Figure 10:
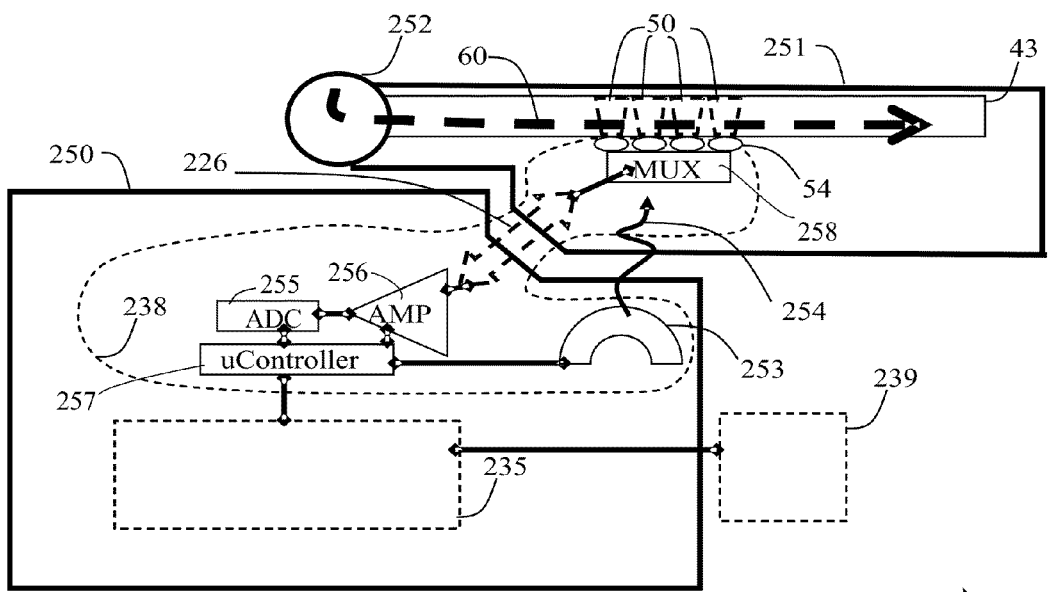
FIG. 10. Schematic view of detection system showing electrical, physical, and flow connections.

A functional schematic of the system is shown in FIG. 10. The system fixture, 250, is designed to mate mechanically and electrically with disposable assay cartridge, 251. The electromagnetic effect sensor detection circuit, 238, is outlined by dashed irregular shape. Some components of this detection circuit are located at least in part on disposable assay cartridge 251, while other components (this subgroup is called the analysis circuit) are located on the fixture 250. An electrical connection between these two mechanical is made using connector 226. Electrical connections are provided between the detection circuit 238, system control 235, and external client, 239. The external client can be a person, another circuit, or a machine, all of which use the data from the system for some analytical purpose.

An electromagnetic effect field excitation source, 253, may be provided, as are electrical connections from it to control circuit 238. Excitation source 253 is designed to impart a specific type of electromagnetic effect energy 254 upon label detection zones 50. This excitation source type can be selected from the group consisting of magnetic field and electric field and photonic. The magnetic yoke 222 in FIG. 9 is an example of a magnetic field source. In order for source 253 to be photonic, it could be an LED, a laser, or an ordinary lamp. Sample source 252 is provided at the beginning of flow path 60, which passes through flow permeable membrane 43 and label detection zones 50 and respective sensors 51, 52, 53, and 54 (only 54 is called out here to minimize clutter).

Figure 11:
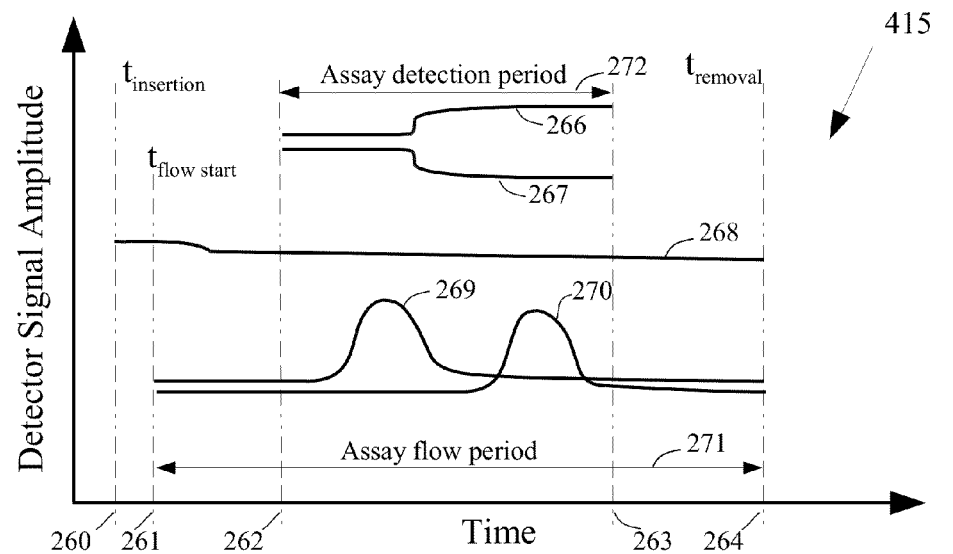
FIG. 11. Representative plot of sensor signal versus time for a variety of assay measurement methods.

FIG. 11 shows how time dependent signal levels in detector circuit 238 are related to key events in some typical label and assay measurement sequences. Disposable assay cartridge 251 is placed in fixture 250 at the time labeled $t_{insertion}$ in FIG. 11 and removed at time $t_{removal}$. A fluid sample is introduced to sample input 252 at time $t_{flow}$ start. The assay flow period begins at $t_{flow}$ start and may continue until $t_{removal}$. The assay detection period represents the period of time that the detector circuit is collecting signals from the sensors. The assay detection period can be at most the entire time between at $t_{insertion}$ and $t_{removal}$ as is shown for detector signal curve 268. This curve is representative of a signal from a reference or background sensor, designed to monitor and compensate for the presence of fluid, changes in temperature and other ambient conditions.

Curve 266 is suggestive of detector results from a binding type assay like that shown in FIG. 3. In this case, the presence of assay analyte causes labels to be bound at label capture sites.

Curve 267 is suggestive of detector results from a competition type assay where the analyte of interest acts to unbind labels that had been bound initially in the label capture site.

Curves 269 and 270 represent a flow rate detection assay where the signal from two different label detection zones are monitored for transients. The time difference between the "humps" in these curves is inversely proportional to the flow rate of labels in the flow stream.

Figure 12:
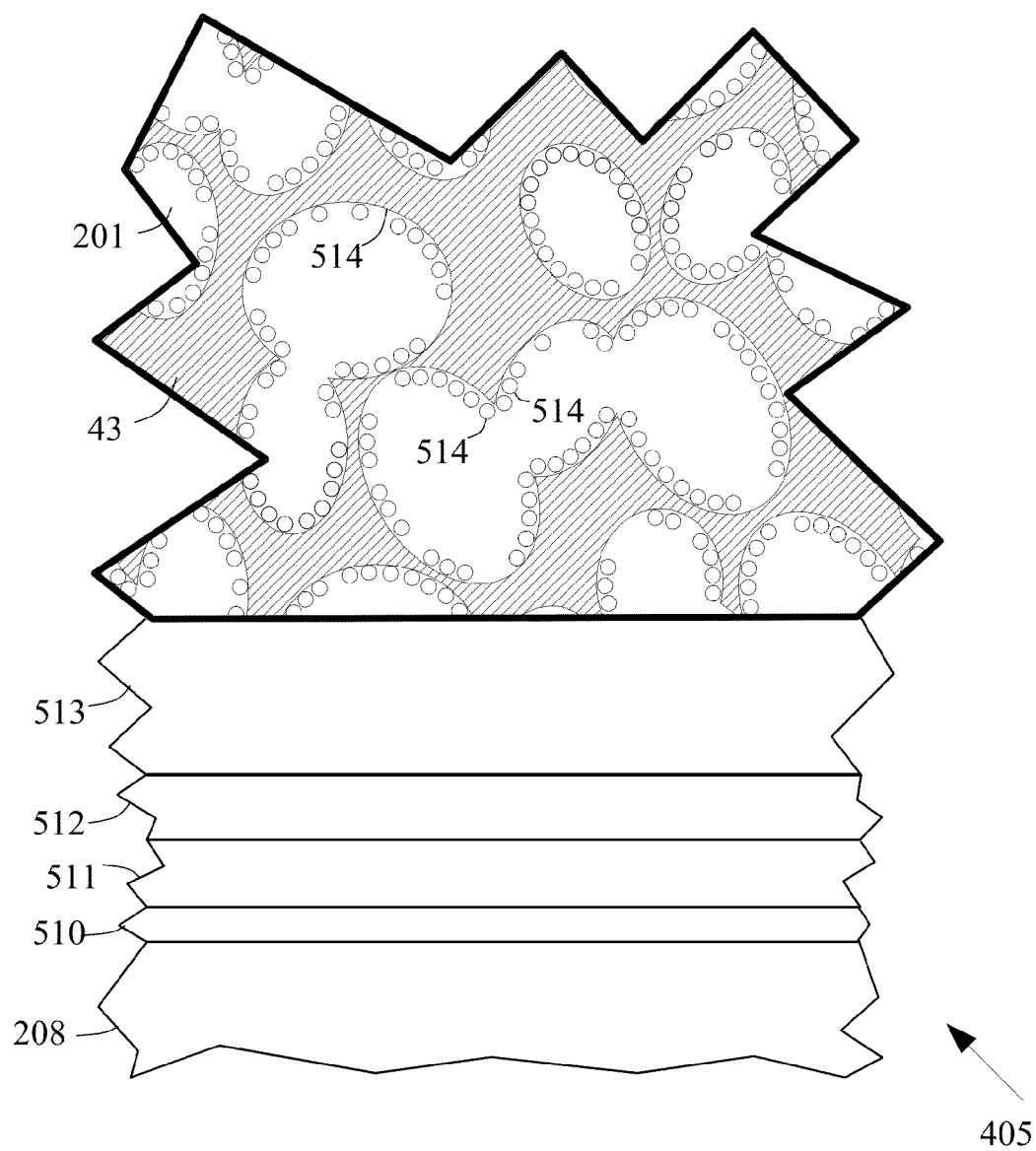
FIG. 12 A close up cross section view of a p-n photodiode beneath a flow permeable membrane. There are fluorescent labels bound to the membrane above the sensor.

FIG. 12 shows a cross section detail of the construction of a photonic type electromagnetic effect sensor. The sensor is formed using standard semiconductor processing on Si substrate 208. This substrate is obtained with a light p-doping. Layer 511 is heavily a doped n+ layer. The junction between substrate 208 and n+ layer 511 is a standard photodiode. This p-n photodiode generates electrical current when photons are incident from above. Additional features can include a photo dye layer 512, clear adhesive layer 513 acrylic available from Adhesives Research, and fluorescent labels 514.

Although the present invention has been described with reference to certain preferred embodiments, workers skilled in the art will recognize that changes of form and detail may be made without departing from the spirit and scope of the invention.

What I claim is:

1. An electromagnetic effect field detection system for measuring labels in a fluid comprising:
    a planar substrate;
    at least one electromagnetic effect field sensor formed on a first surface of said planar substrate;
    a backing structure substantially supporting a second surface of said planar substrate where said second surface is on the opposite side of said planar substrate from said electromagnetic effect field sensor;
    a flow permeable membrane supported substantially on said first surface of said planar substrate and covering said at least one electromagnetic effect field sensor;
    wherein a thinnest dimension of said flow permeable membrane is perpendicular to said first surface of said planar substrate; wherein a length and width of said flow permeable membrane are parallel to said first surface of said planar substrate;
    one or more sensing lanes, each lane comprising;
        a continuous flow path and intended flow direction through interconnected pores of said flow permeable membrane, said continuous flow path being substantially parallel to the length of said flow permeable membrane,
        one or more label detection zones, where said label detection zones are disposed within said flow permeable membrane and positioned directly above said electromagnetic effect field sensor;
    where the surface area of said flow permeable membrane is greater than that of said planar substrate;
    wherein said continuous flow path further comprises features that divert flow by plugging some of said pores in said flow permeable membrane.

2. The system of claim 1 wherein said flow permeable membrane is bonded to the electromagnetic effect field sensor by a layer of adhesive material, and a portion of said flow permeable membrane extends beyond the edge of said planar substrate, in at least one direction.

3. The system of claim 2 further comprising a layer of material with low electrical conductivity interposed between the adhesive layer and the electromagnetic effect field sensor.

4. The system of claim 1 further comprising a layer of material with low electrical conductivity interposed between the electromagnetic effect field sensor and the flow permeable membrane.

5. The system of claim 1 wherein the electromagnetic effect field sensor detects an electromagnetic effect field emitted by a label in one of said label detection zones.

6. The system of claim 1 wherein some portions of said backing structure are substantially flush with said first surface of said planar substrate.

\* \* \* \* \*